United States Patent
Aferzon (10) Patent No.: US 7,588,593 B2
(45) Date of Patent: Sep. 15, 2009

(54) PEDICLE SCREW WITH VERTICAL ADJUSTMENT

(75) Inventor: Joseph Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 317 days.

(21) Appl. No.: 11/406,134

(22) Filed: Apr. 18, 2006

(65) Prior Publication Data

US 2007/0244482 A1   Oct. 18, 2007

(51) Int. Cl.
   *A61B 17/70*   (2006.01)
(52) U.S. Cl. ........................ 606/265; 606/267
(58) Field of Classification Search ......... 606/264–279
   See application file for complete search history.

(56) References Cited

U.S. PATENT DOCUMENTS

| | | | | |
|---|---|---|---|---|
| 5,549,608 | A * | 8/1996 | Errico et al. | 606/264 |
| 5,609,593 | A * | 3/1997 | Errico et al. | 606/276 |
| 5,609,594 | A * | 3/1997 | Errico et al. | 606/276 |
| 5,882,350 | A * | 3/1999 | Ralph et al. | 606/278 |
| 5,885,286 | A * | 3/1999 | Sherman et al. | 606/270 |
| 6,063,090 | A * | 5/2000 | Schlapfer | 606/270 |
| 6,214,012 | B1 * | 4/2001 | Karpman et al. | 606/93 |
| 6,368,321 | B1 * | 4/2002 | Jackson | 606/270 |
| 6,478,798 | B1 * | 11/2002 | Howland | 606/264 |
| RE39,089 | E * | 5/2006 | Ralph et al. | 606/278 |
| 7,121,755 | B2 * | 10/2006 | Schlapfer et al. | 403/77 |
| 7,306,603 | B2 * | 12/2007 | Boehm et al. | 606/279 |
| 7,306,606 | B2 * | 12/2007 | Sasing | 606/279 |
| 2003/0216735 | A1 * | 11/2003 | Altarac et al. | 606/61 |
| 2004/0097933 | A1 * | 5/2004 | Lourdel et al. | 606/61 |
| 2004/0138662 | A1 * | 7/2004 | Landry et al. | 606/61 |
| 2004/0162560 | A1 * | 8/2004 | Raynor et al. | 606/73 |
| 2004/0193160 | A1 * | 9/2004 | Richelsoph | 606/61 |
| 2004/0225289 | A1 * | 11/2004 | Biedermann et al. | 606/61 |
| 2004/0236330 | A1 * | 11/2004 | Purcell et al. | 606/61 |
| 2005/0065517 | A1 * | 3/2005 | Chin | 606/61 |
| 2005/0154389 | A1 * | 7/2005 | Selover et al. | 606/61 |
| 2005/0216003 | A1 * | 9/2005 | Biedermann et al. | 606/61 |
| 2005/0234451 | A1 * | 10/2005 | Markworth | 606/61 |
| 2006/0036244 | A1 * | 2/2006 | Spitler et al. | 606/61 |
| 2006/0095038 | A1 * | 5/2006 | Jackson | 606/61 |
| 2006/0149237 | A1 * | 7/2006 | Markworth et al. | 606/61 |
| 2006/0149241 | A1 * | 7/2006 | Richelsoph et al. | 606/61 |
| 2007/0093826 | A1 * | 4/2007 | Hawkes et al. | 606/61 |
| 2007/0270813 | A1 * | 11/2007 | Garamszegi | 606/61 |
| 2008/0004625 | A1 * | 1/2008 | Runco et al. | 606/73 |
| 2008/0009862 | A1 * | 1/2008 | Hoffman | 606/61 |

* cited by examiner

*Primary Examiner*—Eduardo C Robert
*Assistant Examiner*—Mary Hoffman
(74) *Attorney, Agent, or Firm*—Hoffmann & Baron, LLP (57) ABSTRACT

An apparatus for rigid fixation of individual vertebra to the stabilizing rod. It consists of an anchor secured to the vertebra and a connector with multiple degrees of freedom linking each anchor to a rod. Pressure from the rod against a connector engages internal constricting mechanism and eliminates movement within the connection. This results in rigid fixation between individual anchors and the rod.

15 Claims, 8 Drawing Sheets

PEDICLE SCREW WITH VERTICAL ADJUSTMENT

FIELD OF INVENTION

This invention relates to a spinal fixation device. More specifically, the present invention relates to an implant bridging together two or more vertebra by anchoring to the posterior vertebral arch and pedicles.

BACKGROUND

Spinal fusion is utilized to correct painful movement across degenerated or unstable spinal segment and is supplemented by fixation with screws. Screws are commonly placed through the posterior vertebral arch. Multiple fixation targets have been used in the past including facets, spinal processes, lamina, transverse processes, lateral masses and pedicles. Currently fixation through the pedicles offers the most robust purchase and is utilized when possible.

Screws are implanted from the back to the front of the vertebra with one screw inserted per each side per vertebra. Individual screws have to be rigidly linked to eliminate movement between corresponding vertebras. (U.S. Pat. No. 5,474, 555 Puno et al.). Anatomy of individual patient makes it difficult and often impossible to line up pedicle screws in one plane. Screws project with variable medial-lateral displacements and different angulations. This places significant challenges on the mechanical design of the linking system. These complex mechanisms with multiple joints have to be manipulated in a deep wound restricted by muscle and soft tissue.

Most of the available systems can be broken into one of three groups: plating system (U.S. Pat. No. 4,611,581); top loading rod system (U.S. Pat. Nos. 4,805,602, 5,360,431) and side loading rod system (U.S. Pat. No. 5,261,909).

The top loading rod systems utilizes a seat for the rod that projects along the screw trajectory and forms a ball and socket joint with the spherical screw head. It offers several degrees of freedom about the screw axis: (i) 30-40 degrees of angular deflection from the screw axis (ii) 360 degrees of rotation about the screw axis. Any further adjustments have to be gained by contouring the rod to fit into the rod receptacle of the seat. These systems offer advantages when the exposure is directly over the screw such as in muscle splitting or minimally invasive approaches.

In a standard midline approach screws project out into the soft tissue at the lateral extreme of the exposure. Top loaded systems require manipulation at this lateral extreme and side loading rod system can offer advantages in these circumstances. In side loading rod systems connectors run perpendicular to the screw trajectory and the rod is placed on the side of the screw toward the center of exposure U.S. Pat. No. 5,261,909).

SUMMARY OF THE INVENTION

The claimed invention offers a number of significant advantages over existing art.
1. Screw-rod articulation functions as a rotating and pivoting joint and not a ball and socket joint characteristic of top loading systems. It allows much greater angular deflection (over 90 degrees) while still matching full 360 degree rotation.
2. Clamping mechanism allows substantial vertical travel along the screw trajectory contributing to additional degrees of freedom. This adds substantial flexibility particularly when more then 3 screws need to be connected.
3. Connector can be snapped onto the screw head after screw is placed into the bone. This keeps hardware profile minimal and improves exposure for delivery of graft material. It also allows for all the connectors and rods to be assembled outside of the wound. This is particularly valuable in small direct exposures characteristic of the minimally invasive approach.
4. This system can be utilized both as a top loading and side loading system which can not be matched by the currently available art.

In accordance with an embodiment of the present invention, there is provided device for fixation of at least one spinal segment comprising a rod, at least two bone screws and at least two connectors said connectors having a rod receiver, screw clamp, compression spacer and a tightening nut. The rod receiver has at one end a channel with threaded walls accepting the rod and the tightening nut, with the opposite end sliding over the screw clamp. The screw clamp has the articulating end opposite to the sliding portion and fitting over the bone screw said bone screw having a threaded portion imbedded into the bone with protruding articulating portion coupled with the screw clamp and allowing for a pivoting and rotational motion in uncompressed state but immobilized by compression from the compression spacer. The compression spacer is housed within rod receiver, engaged by the rod pressed into the rod receiver and clamping on the screw clamp which in turn clamps on articulation between screw clamp and bone screw

DETAILED DESCRIPTION

Figure 1:
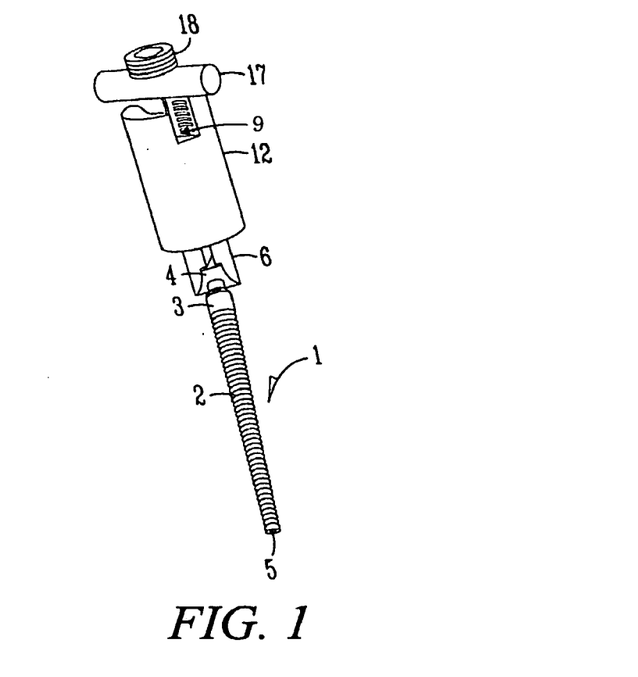
FIG. 1 Preferred embodiment of the invention showing screw (1), screw clamp (6), compression spacer (9), rod (17) and nut (18)
Figure 1A:
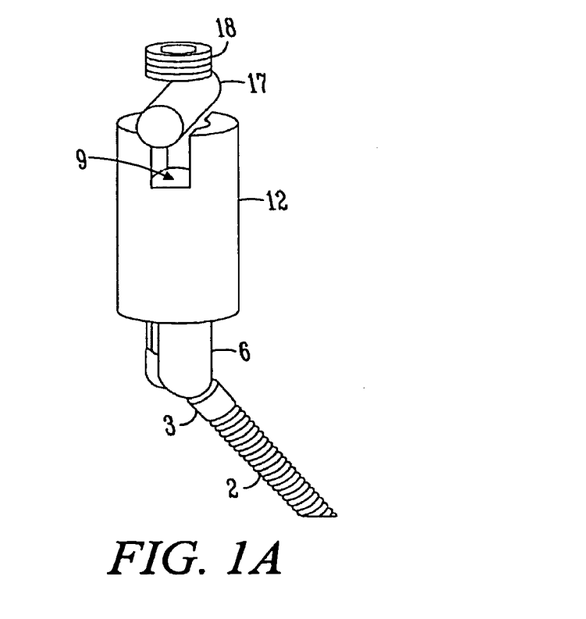
FIG. 1a Different orientation of the preferred embodiment of the invention showing screw (1), screw clamp (6), compression spacer (9), rod (17) and nut (18).

In its preferred embodiment device consists of a screw, screw clamp, rod receiver, compression spacer, rod and nut (FIG. 1).

Figure 2:
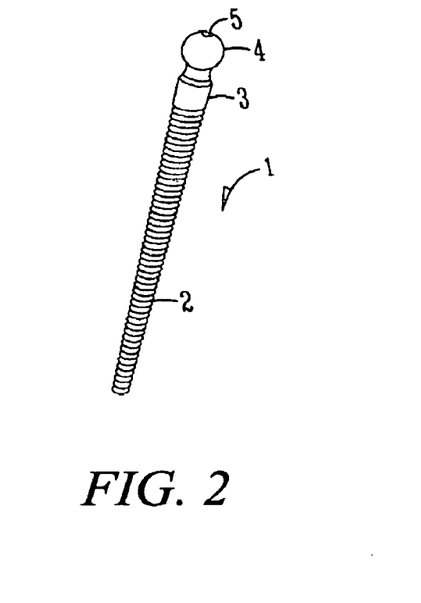
FIG. 2 Bone screw consisting of threaded portion (2), protruding shaft (3) and spherical head (4). Please notice the channel (5) through the center of the screw.
Figure 3:
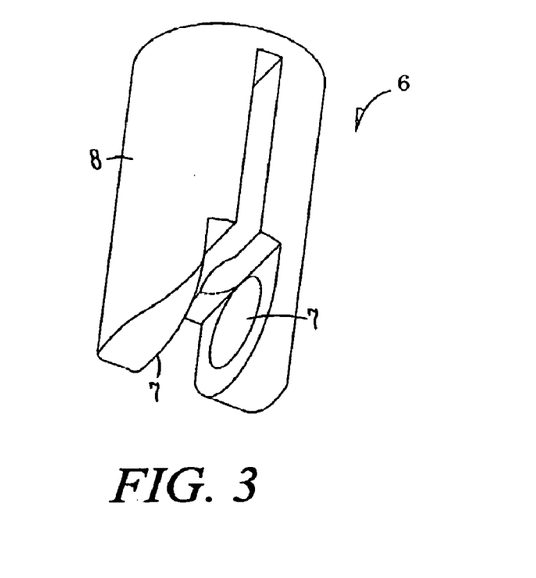
FIG. 3 Preferred embodiment of the screw clamp consisting of a cylindrical compressible shaft (8) and articulating end (7).
Figures 4, 5:
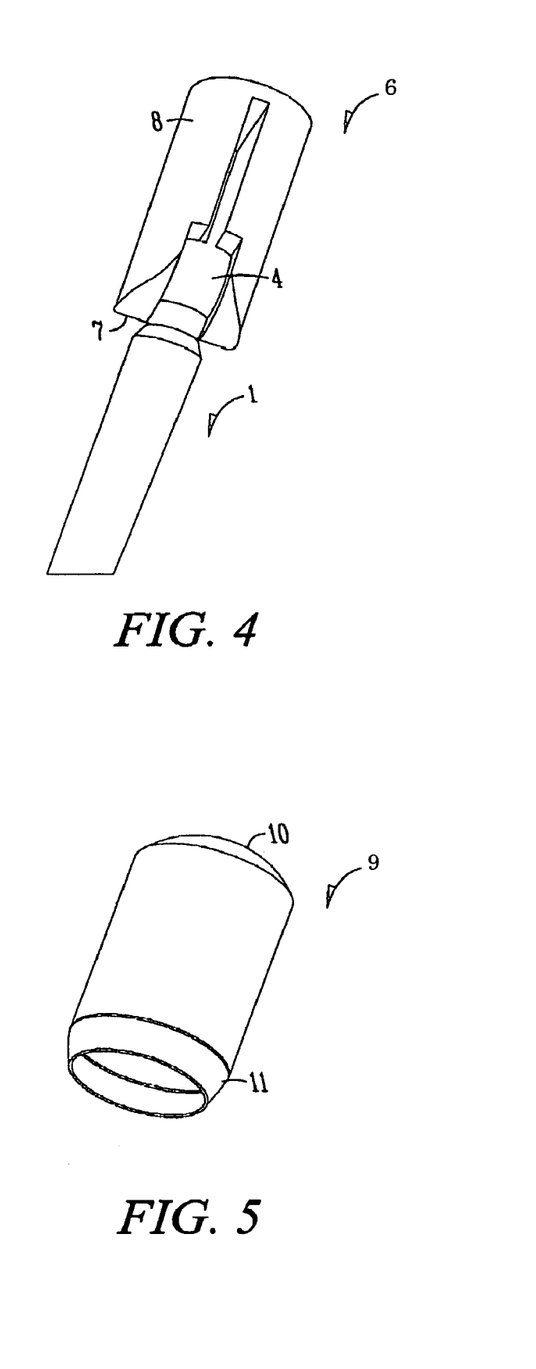
FIG. 4 Articulation between screw head (4) and articulating end (7) of the screw clamp. Notice that this articulation allows only pivoting motion and is not a ball-socket joint.
FIG. 5 One of the embodiments of the compression spacer (9) with contact dome (10) which is depressed by the rod (17) when its locked, and constricting tube (11) deformed by the tapered section of the rod receiver (16).

Screw has a long threaded portion placed into the bone and a protruding cylindrical shaft with a spherical head (FIG. 2). A compressible cylindrically shaped screw clamp of substantial thickness (FIG. 3) has a spherical cut-out at one end such that it fits precisely over the screw head (FIG. 4). It pivots about the screw head with angle of deflection greater then ninety degrees and 360 degrees of revolution through the entire range of deflection.

Figure 6:
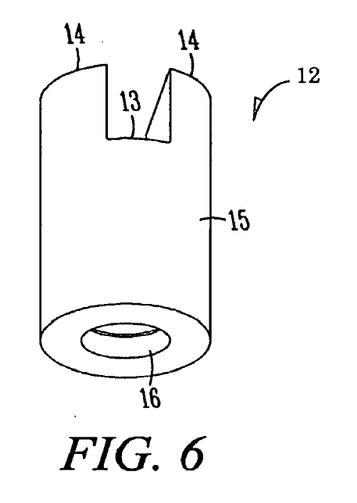
FIG. 6 Preferred embodiment of the rod receiver (12) consisting of the seat (13) for the rod, threaded extensions (14) which accept a nut (18), travel tube (15) and tapered end (16).
Figure 7:
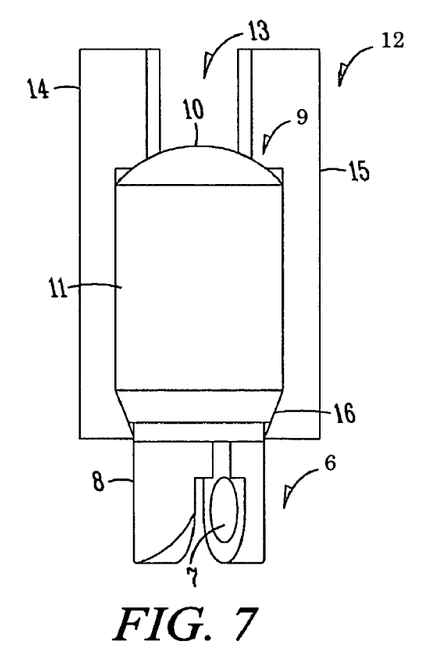
FIG. 7 Assembly consists of screw clamp (6), compression spacer (9) and rod receiver (12).
Figure 8:
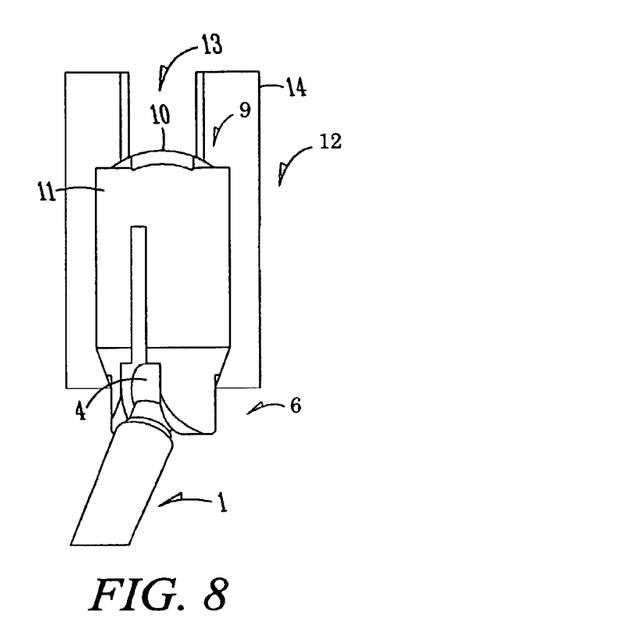
FIG. 8 Preferred embodiment of the invention with compression spacer (9) and rod receiver (12) rendered transparent to demonstrate the entire assembly.
Figure 9:
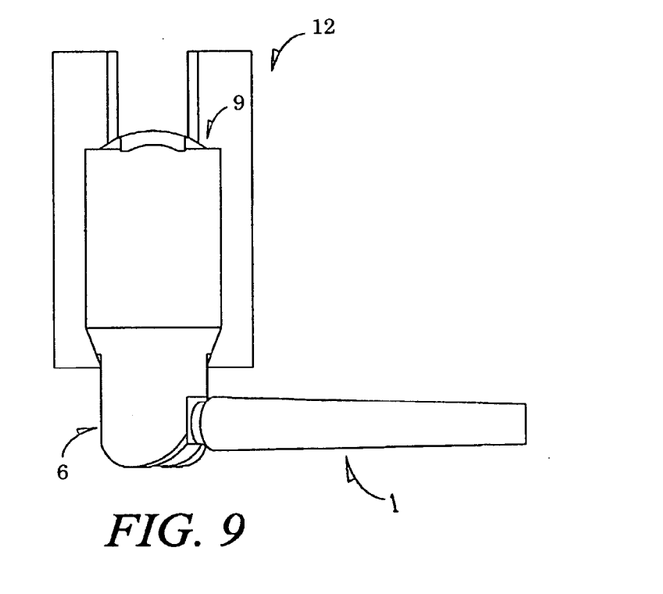
Figure 10:
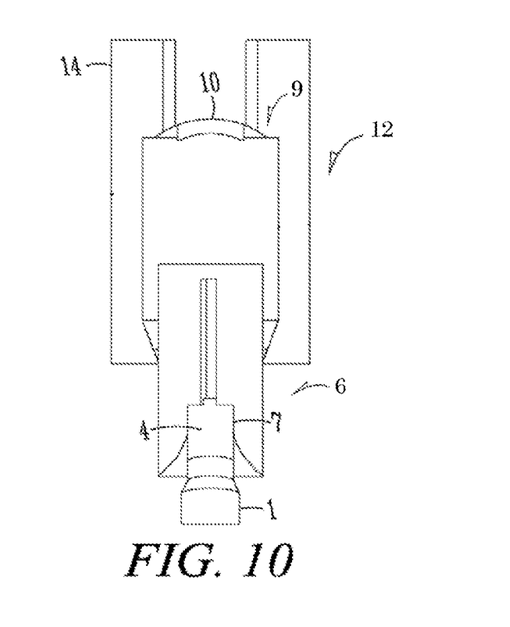
FIG. 10 Assembly demonstrates vertical travel of screw clamp (6) within the rod receiver (12). Please compare to Pic 8. Please note that compression by compression spacer (9) will be transferred to screw clamp (6) over a wide range of vertical travel.
Figure 11:
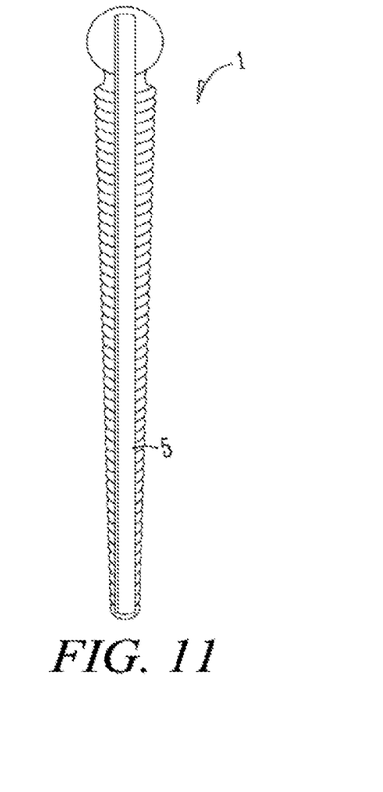
FIG. 11 Bone screw (1) with central channel (5).
Figure 12:
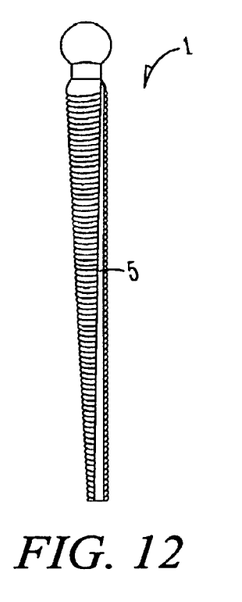
FIG. 12. Bone screw (1) with off-center channel (5).

Screw clamp (FIG. 6) tightly fits into cylindrical assembly consisting of the rod receiver and compression spacer (FIG. 7). Rod receiver has a travel tube with a tapered end which fits over the screw clamp. The other end forms the seat for the rod bounded by threaded walls (FIG. 8). Up and down movement of the screw clamp within the rod receiver allows for a vertical adjustment. Compression clamp is a deformable component fitting within the travel tube of the rod receiver (FIG. 5). It has a contact dome extending into the seat of the rod receiver. Pressure from the rod locked into the seat by a threaded nut, displaces the compression spacer into the tapered end of the travel tube. The resulting deformation of the compression spacer transfers compressive force onto the screw clamp. This fixes the screw head within the screw clamp and prevents any travel of the screw clamp within the travel tube. This process is repeated for each screw in the assembly.

Figure 13:
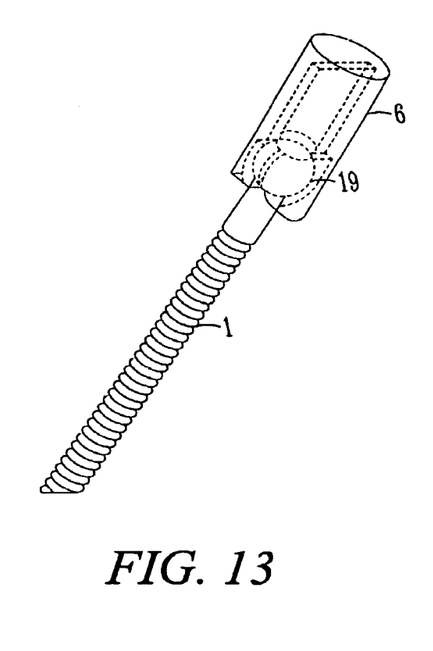
FIG. 13 Alternative embodiment of the screw (1) and screw clamp (6) articulation with compressible spherical spacer (19) threaded over the cylindrical screw shaft(3).
Figure 14:
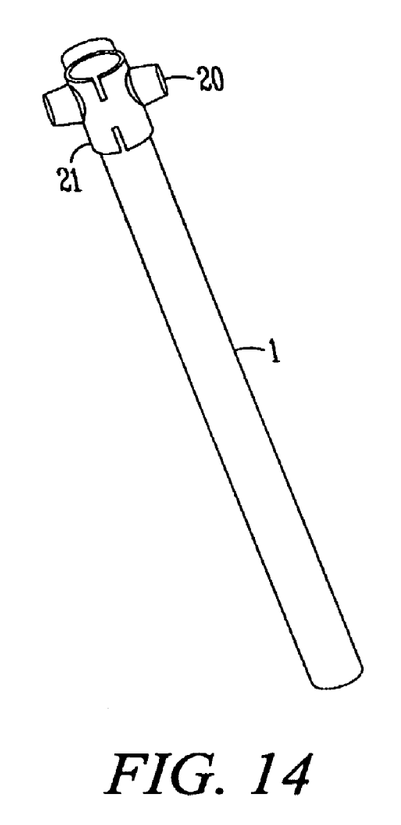
FIG. 14 Alternative embodiment of the screw (1) and screw clamp articulation. Screw clamp would be modified to fit over the projections (20) of the compressible T-spacer (21).

Alternative embodiments of the screw shaft and screw clamp articulation which enable pivoting and rotational motion are possible.
(FIG. 13, FIG. 14).

BRIEF DESCRIPTION OF DRAWINGS

Also note the screw clamp (6) and the screw (1). Note that if deformable compression spacer (9) is pressed into the rod receiver (12) the tapered configuration at the bottom of the rod receiver will constrict corresponding area of the compression spacer, which in turn will transmit compressive forces to the articulation between screw clamp (6) and a screw (1).

FIG. 9 (Landscape orientation)

Demonstrates 90 degrees deflection angle (potentially >90 degrees) between screw (1) and screw clamp (6).

The invention claimed is:

1. An assembly to secure a spinal segment including a plurality of vertebrae, the assembly comprising:
    at least one stabilizing rod;
    a plurality of vertebral anchors, each vertebral anchor having a first end to engage a vertebra and a connecting head end; and
    a plurality of connectors to secure the plurality of vertebral anchors to the at least one stabilizing rod, each connector comprising:
        an anchor clamp including a plurality of receptacles to receive the connecting head end of a vertebral anchor and to provide angular deflection and rotation of the anchor clamp with respect to the vertebral anchor;
        a compression spacer including a top, a tube and a tapered end, the tapered end to receive at least a portion of the anchor clamp within the tube, the tube to provide vertical travel and rotation of the anchor clamp with respect to the tube; and
        a rod receiver to house the compression spacer, the rod receiver including a first end having a transverse channel to receive the at least one stabilizing rod in the channel, the channel having threaded walls to receive a tightening nut, the rod receiver including a second end having a taper to receive the portion of the anchor clamp within the compression spacer.

2. The assembly of claim 1, wherein the at least one stabilizing rod comprises a first stabilizing rod to be disposed on a first side of the spinal segment and a second stabilizing rod to be disposed on a second side of the spinal segment.

3. The assembly of claim 2, further comprising a transverse bridging member to link the first stabilizing rod and the second stabilizing rod.

4. The assembly of claim 1, wherein the first end of the vertebral anchor is a screw and the connecting head end of the vertebral anchor is of a substantially spherical shape or a cylindrical shape.

5. The assembly of claim 4, wherein the vertebral anchor includes a channel through a central axis of the screw and the connecting head end.

6. The assembly of claim 4, wherein the vertebral anchor includes an off-center channel extending from a tip of the screw through to a side of the screw.

7. The assembly of claim 1, wherein the vertebral anchor comprises a means for handling the vertebral anchor to engage a vertebra.

8. The assembly of claim 7, wherein the means for handling the vertebral anchor includes one or more protrusions and one or more surface indentations on the vertebral anchor.

9. The assembly of claim 1, wherein the threaded walls of the channel include extensions to project above a skin surface.

10. The assembly of claim 9, wherein the at least one stabilizing rod includes one or more protrusions and one or more surface indentations at each end of the at least one stabilizing rod.

11. The assembly of claim 1, wherein the vertebral anchor is one of a lamina hook, a transverse process hook, a facet screw, and a facet bolt.

12. The assembly of claim 1, wherein the connecting head end of the vertebral anchor has one of an uneven knurled surface and a smooth surface.

13. The assembly of claim 1, wherein the receptacles of the anchor clamp have one of an uneven knurled surfaces and smooth surfaces.

14. A connector to secure a vertebral anchor to a stabilizing rod, the connector comprising:
    an anchor clamp including a plurality of receptacles to receive a connecting head end of the vertebral anchor secured to a vertebra and to provide angular deflection and rotation of the anchor clamp with respect to the secured vertebral anchor;
    a compression spacer including a top, a tube and a tapered end, the tapered end to receive at least a portion of the anchor clamp within the tube, the tube to provide vertical travel and rotation of the anchor clamp with respect to the tube;
    a rod receiver to house the compression spacer, the rod receiver including a first end having a transverse channel to receive the stabilizing rod in the channel and threaded walls to receive a tightening nut, the rod receiver including a second end having a taper to receive the portion of the anchor clamp within the compression spacer housed in the rod receiver.

15. An articulation device for fixation of a vertebra to a stabilizing rod, the device comprising:
    a vertebral anchor having a first end to engage the vertebra and having a connecting head end; and a connector to secure the vertebral anchor to the stabilizing rod, the connector comprising:
- an anchor clamp including a plurality of receptacles to receive the connecting head end of the vertebral anchor and to provide angular deflection and rotation of the anchor clamp with respect to the vertebral anchor;
- a compression spacer including a top, a tube and a tapered end, the tapered end to receive at least a portion of the anchor clamp within the tube, the tube to provide displacement and rotation of the anchor clamp with respect to the tube; and
- a rod receiver to house the compression spacer, the rod receiver including a first end having a transverse channel to receive the stabilizing rod in the channel and threaded walls to receive a tightening nut, the rod receiver including a second end having a taper to receive the portion of the anchor clamp within the compression spacer housed in the rod receiver;
- wherein the threading of the tightening nut within the threaded walls causes the stabilizing rod to displace the compression spacer into the taper of the second end of the rod receiver and to secure the compression spacer within the rod receiver, the displacement of the compression spacer causing a compressive force on the anchor clamp that deforms the plurality of receptacles about the vertebral anchor to secure the vertebral anchor within the anchor clamp and to secure the anchor clamp within the compression spacer.

* * * * *